US00PP32440P2

(12) United States Plant Patent
Higaki

(10) Patent No.: US PP32,440 P2
(45) Date of Patent: Nov. 10, 2020

(54) ***HYDRANGEA* PLANT NAMED 'BCHY-15.008'**

(50) Latin Name: ***Hydrangea macrophylla* (Thunb.)**
Varietal Denomination: BCHY-15.008

(71) Applicant: Harrison Higaki, San Mateo, CA (US)

(72) Inventor: Harrison Higaki, San Mateo, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days.

(21) Appl. No.: 16/602,178

(22) Filed: Aug. 21, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48
See application file for complete search history.

*Primary Examiner* — Anne Marie Grunberg
(74) *Attorney, Agent, or Firm* — James R. Cypher; Charles R. Cypher

(57) ABSTRACT

A new and distinct cultivar of *Hydrangea macrophylla* (Thunb.) plant named 'BCHY-15.008' originated as a controlled cross between varieties. The variety 'BCHY-15.008' has attractive inflorescences with sepalous florets with attractive sepal pigmentation and good commercial characteristics.

5 Drawing Sheets

Botanical classification: *Hydrangea macrophylla* (Thunb.) 'BCHY-15.008'.

Variety denomination: 'BCHY-15.008'.

BACKGROUND OF THE INVENTION

This invention relates to a new and distinct cultivar of the Saxifragaceae family. The botanical name of the plant is *Hydrangea macrophylla* (Thunb.) 'BCHY-15.008'.

The new cultivar originated as a seedling from a controlled cross between a variety known to the inventor as 'BC7.12' which was the seed parent and the unpatented variety known as 'Rotdrossel' which was the pollen parent. 'BC7.12' was the subject of U.S. patent application Ser. No. 13/986,047 which issued as U.S. Plant Pat. No. 25,677. 'BC7.12' originated as a seedling from a controlled cross between the unpatented variety known as 'LK49' which was the seed parent and a commercial variety known as 'Venedig' to the inventor which may be the subject of U.S. Plant Pat. No. 10,928 and registered as 'Venice Raven'. 'Venedig' was the pollen parent of that cross. 'LK49' is relatively compact plant with wiry stems, relatively small leaves, relatively small sepalous florets, and inflorescences that are resistant to being damaged by conditions in commercial coolers. The applicant is unaware as to whether the commercial variety known as 'Rotdrossel' is the subject of a patent in the United States or a foreign country or protected as a plant variety in the United States or a foreign country. No observations of the parent 'Rotdrossel' were made.

The variety 'BCHY-15.008' has sepalous florets with uniform sepal pigmentation at maturity and good commercial characteristics, including strong stems, a propensity to branch when pinched and a propensity to set infloresences on each stem and lateral branch. The color of the sepals changes as the plant ages. The plant is similar to U.S. Plant Pat. No. 23,757 entitled *Hydangrea* Plant named 'BC6.1'. Below is a table comparing the new variety to similar varieties.

TABLE 1

| | New Variety 'BCHY-15.008' | U.S. Plant Pat. No. 25,677 'BC7.12' |
|---|---|---|
| Leaf size | 10 cm wide × 15 cm long | 9 cm × 16.5 cm |
| Plant height | 13" in 6" pot. | 17" in 6" pot. |
| Stem strength | Strong | Stems are strong. |
| Sepal Pigmentation | Certain plants treated with aluminum: upper sides of sepals are R.H.S. 71 A (red-purple group), and under sides of sepals are R.H.S. 72 B (red-purple group). Plants not treated with aluminum: upper sides of sepals are R.H.S 61 B (red-purple group), and under sides are R.H.S. 70 C (red-purple group). | Upper side of sepals is R.H.S. 67 A (red - purple group); Under side of sepals is R.H.S. 68 A (red-purple group). |
| Sepalous Floret Size - Diameter | 70 mm | 60 mm |

| | U.S. Plant Pat. No. 23,757 'BC6.1' | Commerical variety 'Venedig' which may be U.S. Plant Pat. 10,928 'Venice Raven' |
|---|---|---|
| Leaf size | 13 cm wide × 16 cm long | 11 cm wide × 15.5 cm long - source U.S. Plant Pat. No. 10,928 |
| Plant height | 15" in 6" pot | 12" in 6" pot - observed controls grown alongside 'BC6.1'. |
| Stem strength | Stems are strong but benefit from being staked | Strong - observed controls grown alongside 'BC6.1'. |

TABLE 1-continued

| | | |
|---|---|---|
| Sepal Pigmentation | Upper sides of sepals are R.H.S. 86 A (violet group); Under sides of sepals are R.H.S. 88 D (violet group) | Upper side of sepals is R.H.S. 84 A (violet group). Under side of sepals is R.H.S. 85 A (violet group) observed controls grown alongside 'BC6.1'. |
| Sepalous Floret Size - Diameter | 60 mm to 70 mm | 70 mm - observed controls grown alongside 'BC6.1'. |

The new cultivar 'BCHY-15.008' has been successfully asexually reproduced under controlled environmental conditions at a nursery in Half Moon Bay, Calif. under the direction of the inventor with its distinguishing characteristics remaining stable.

Asexual reproduction was first accomplished when vegetative cuttings were used from the initially selected plant. Examination of asexually reproduced, successive generations grown in Half Moon Bay, Calif. show that the combination of characteristics as herein disclosed for 'BCHY-15.008' remains firmly fixed.

DESCRIPTION OF THE DRAWINGS

The accompanying drawings consist of color photographs that show the typical plant form at 1 year when grown in a commercial nursery and forced to bloom, including the inflorescence, foliage, and sepals.

DESCRIPTION OF THE NEW PLANT

Figure 1:
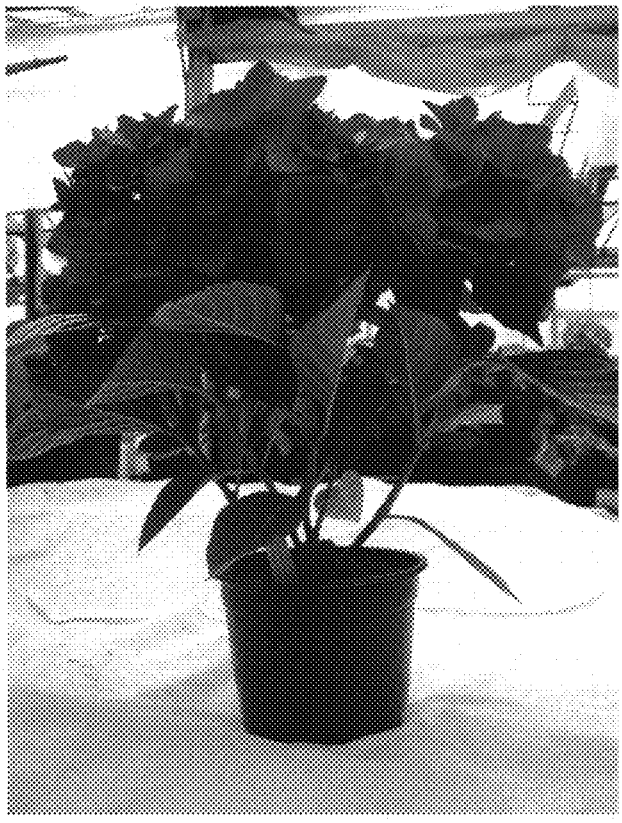
FIG. 1 is a side view of an entire plant treated with aluminum showing its form, growth habit, dark green foliage, inflorescence, and the color of its sepals.
Figure 2:
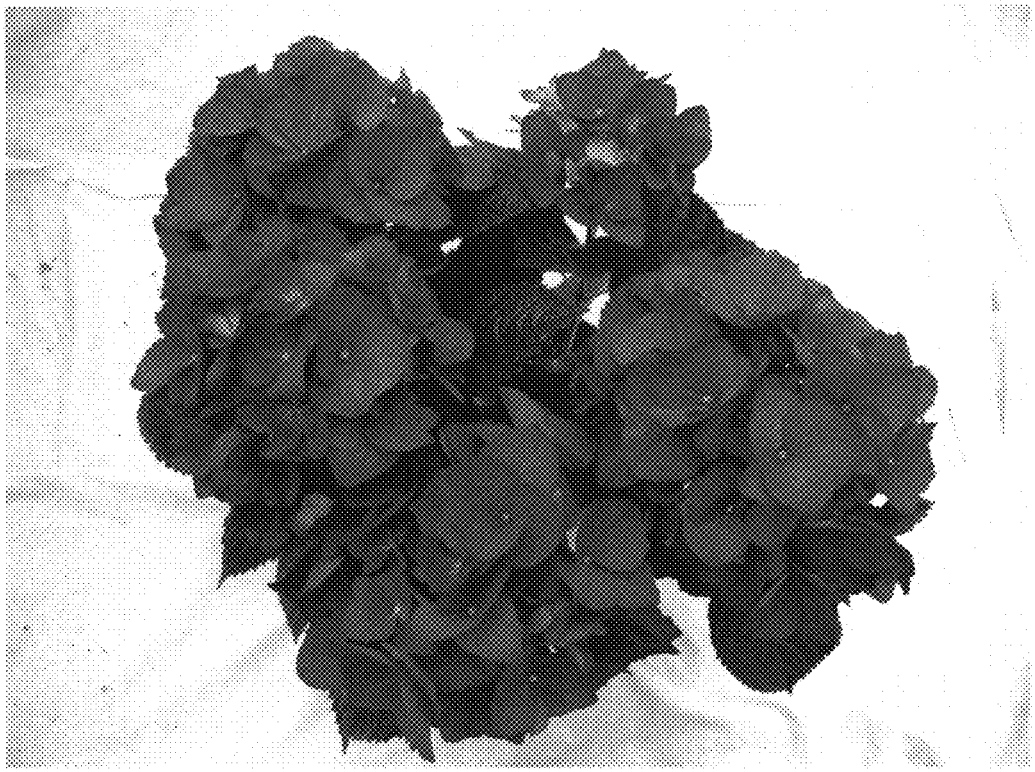
FIG. 2 is a top view of an entire plant treated with aluminum showing its form, growth habit, dark green foliage, inflorescence, and the color of its sepals.
Figure 3:
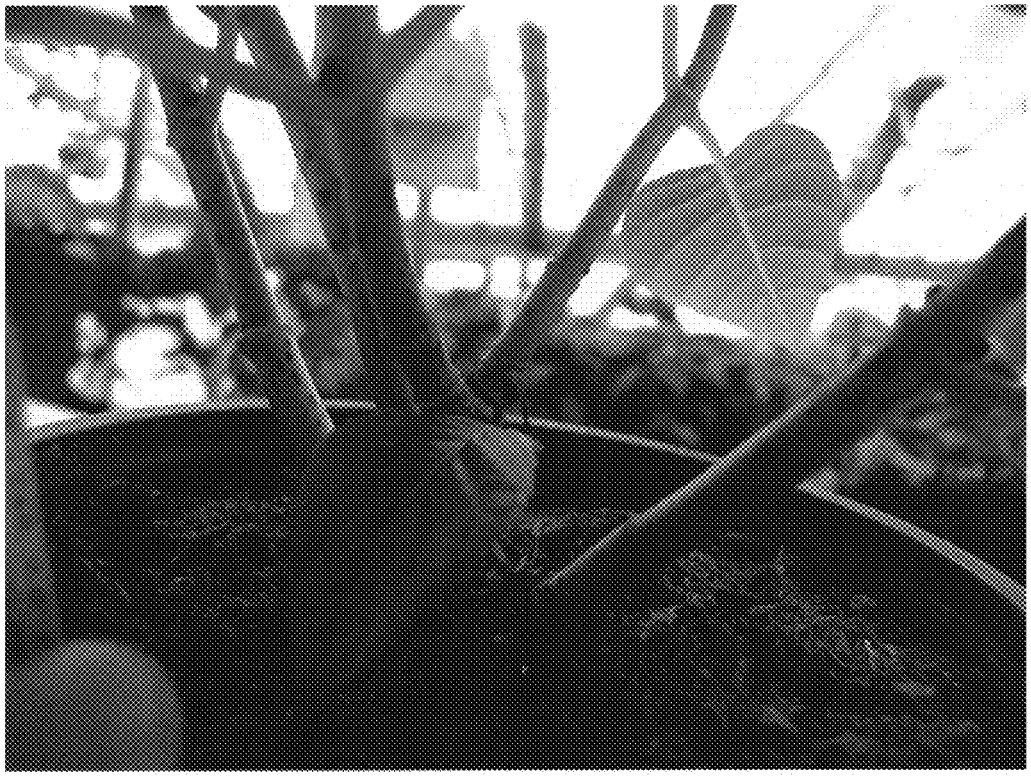
FIG. 3 is a view of the base of the plant treated with aluminum.
Figure 4:
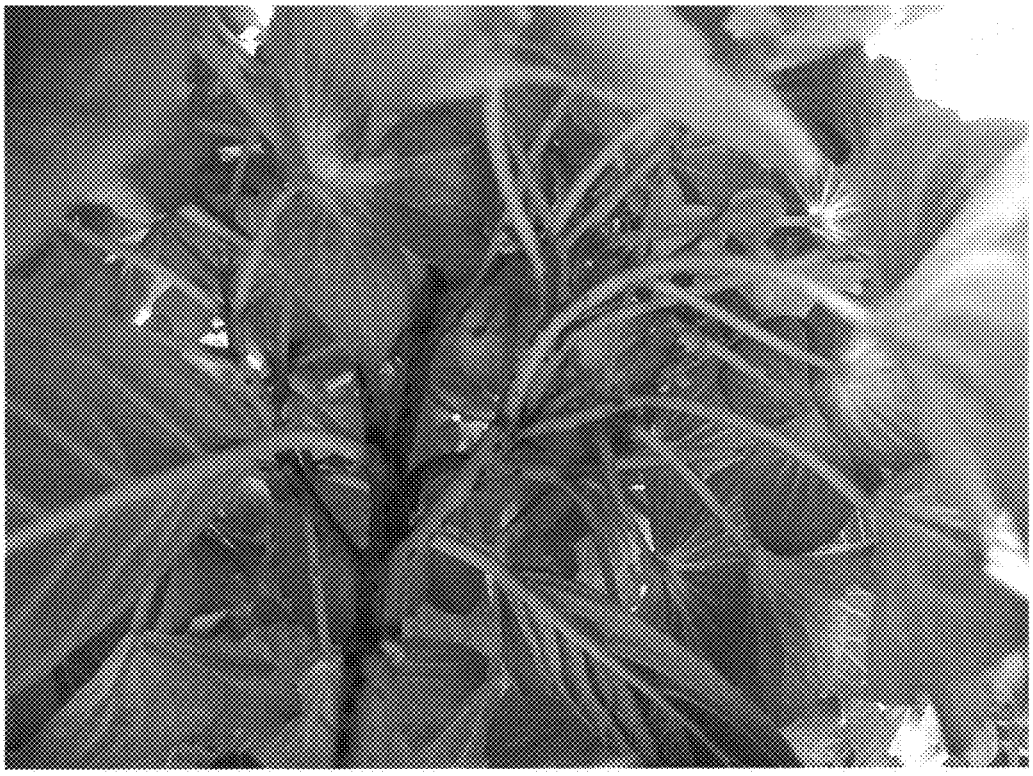
FIG. 4 is a close-up view of the underside of a panicle of a plant treated with aluminum.
Figure 5:
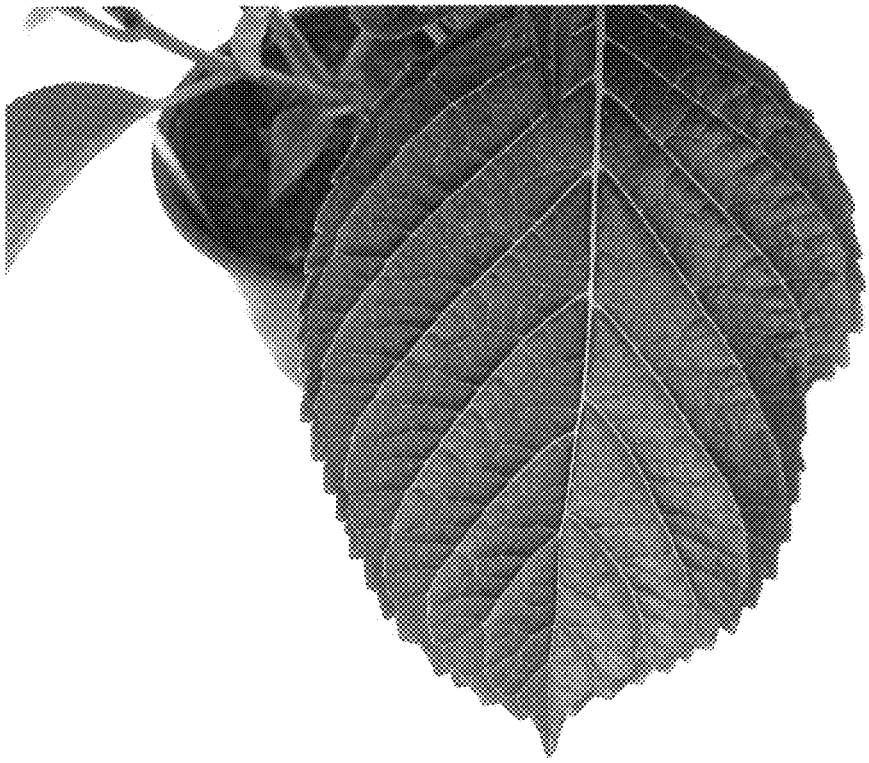
FIG. 5 is a close-up view of the adaxial surface of a mature leaf of a plant treated with aluminum.
Figure 6:
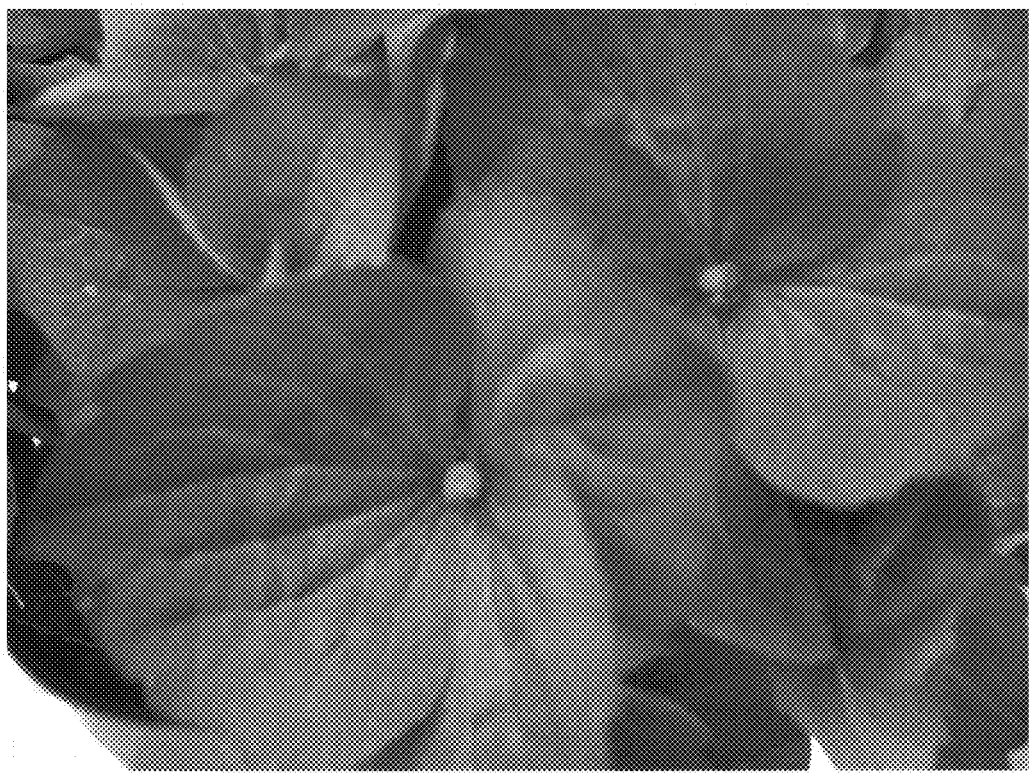
FIG. 6 is a close-up view of the upper side of the inflorescence of the new variety treated with aluminum.
Figure 7:
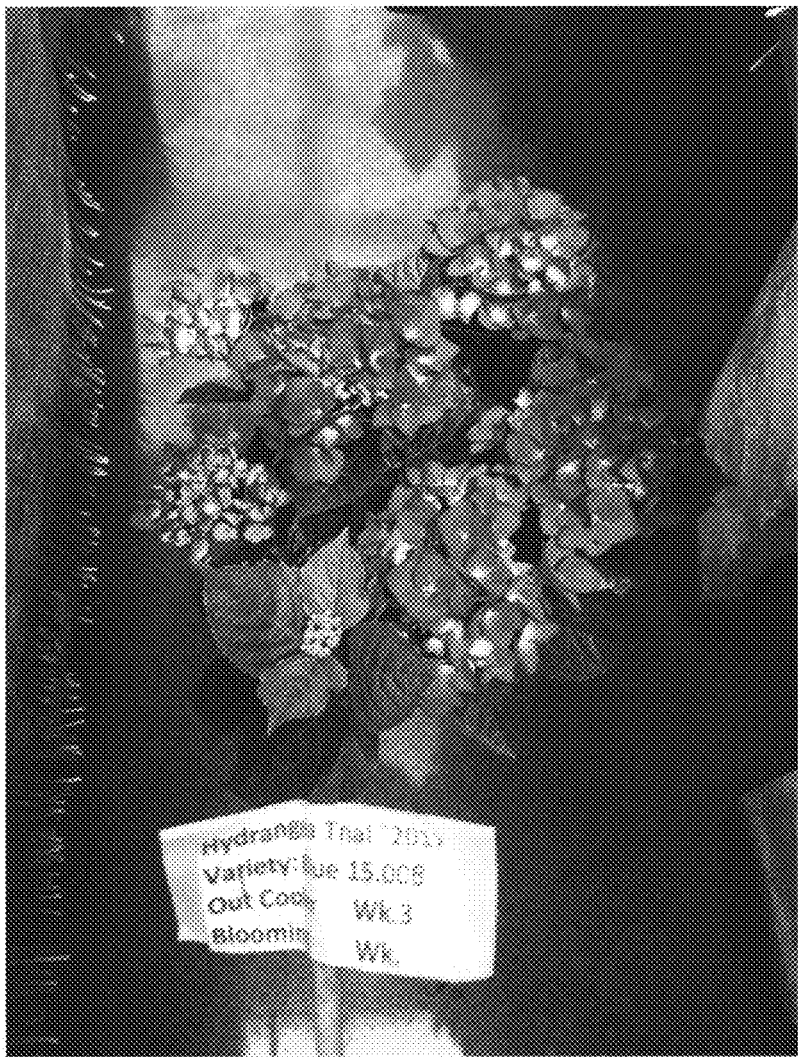
FIG. 7 is at top view of an entire plant treated with aluminum grown in a different cycle than the plant shown in FIGS. 1-6.
Figure 8:
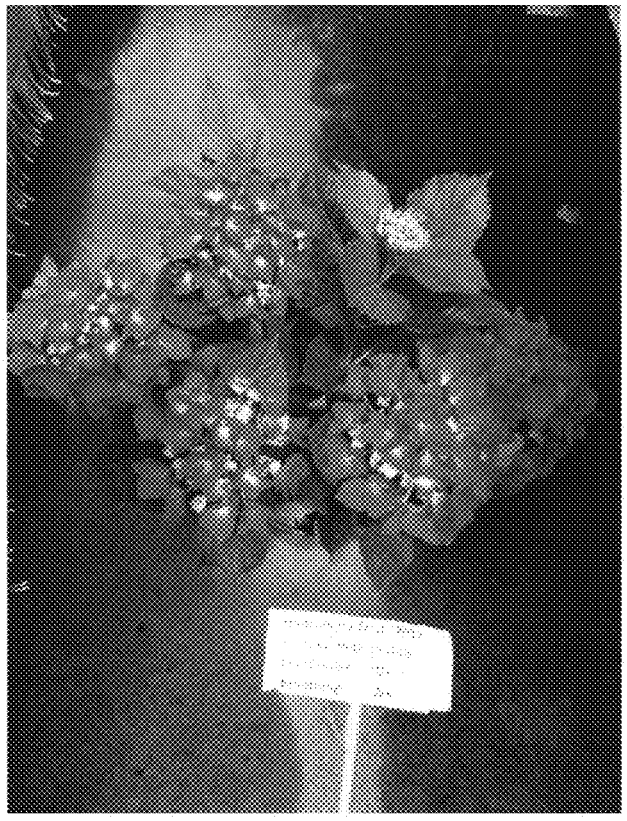
FIG. 8 is at top view of an entire plant not treated with aluminum grown in a different cycle than the plant shown in FIG. 9
Figure 9:
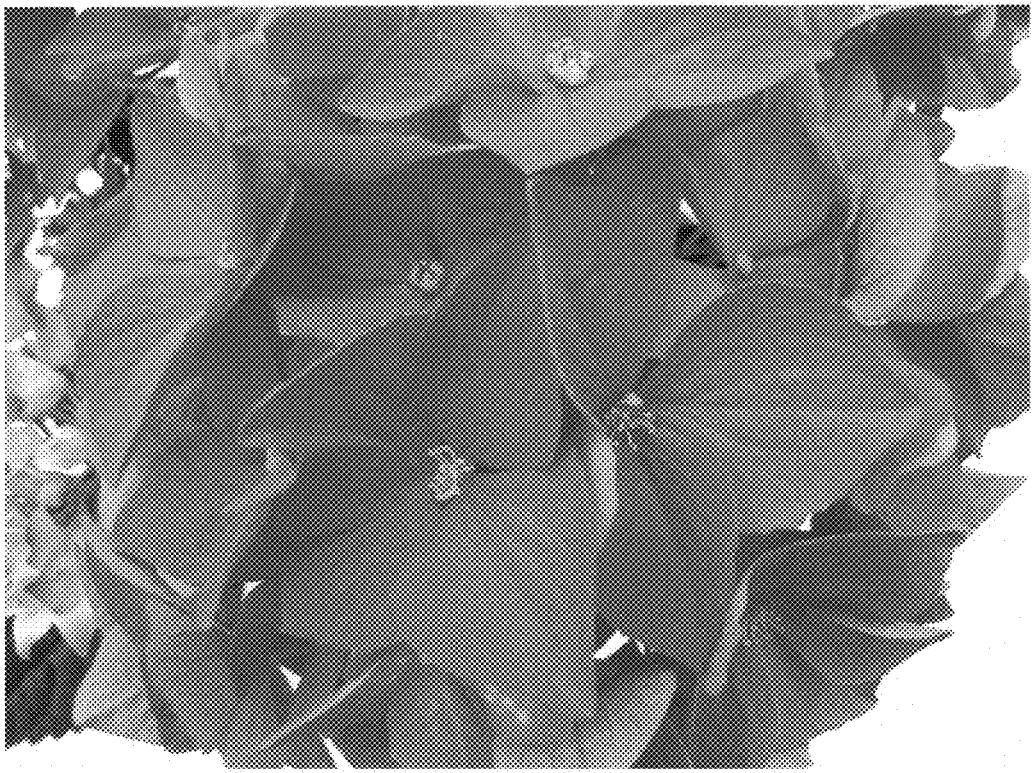
FIG. 9 is a close-up view of the upper side of an inflorescence of a plant not treated with aluminum.

The plants described are approximately a year old. The plant started out as cuttings, used from the stem of a grown plant. The plants shown were pinched early in their development to promote lateral branches. As noted for some of the plants pictured the soil was periodically treated with aluminum to produce a different pigmentation. The plant shown in FIGS. 8 and 9 were not treated aluminum. The plants shown in FIGS. 7 and 8 were grown in a different cycle and under different conditions than the plants shown in FIGS. 1-6 and 9. The plants shown in FIGS. 1-6 and 9 were grown in the same growing cycle. All measurements and color determinations provided for plants grown with aluminum treatments are based on the plants grown in the same cycle and under the same conditions as the plant shown in FIGS. 1-6. All measurements and color determinations provided for plants grown without aluminum treatments are based on the plants grown in the same cycle and under the same conditions as the plant shown in FIG. 9. All measurements and characterizations and color determinations apply to both plants treated with aluminum and those not treated with aluminum unless otherwise noted.

'BCHY-15.008' has not been observed under all possible environmental conditions. The phenotype may vary significantly with variations in environment such as temperature, light intensity, treatment with aluminum and day length. Color determinations were made with The Royal Horticultural Society (R.H.S.) Colour Chart, developed in association with the Flower Council of Holland, located in Lieden. The plant:

*Origin.*—Controlled cross. The new cultivar originated as a seedling from a controlled cross between the patented variety known as 'BC7.12'—U.S. Plant Pat. No. 25,677—which was the seed parent, and the commercial variety 'Rotdrossel' which was the pollen parent.

*Form.*—Upright, non-climbing compact shrub. The mature plant with a mature inflorescence that is ready for sale is approximately 13" high and has a diameter of 15" when grown in a 6" pot with appropriate soil amendments.

*Growth.*—Upright, vigorous growth habit. Inflorescence is medium to large. The plant branches easily with shoots forming at the base of the plant. Lateral branches are similar in appearance and form to the main stems.

*Stems.*—Lenticels are present. Stem lengths are approximately 9". Fasciation is absent. Lenticels are R.H.S. 86 A (violet group) and are 1 to 3 mm long. The surface of young stems is glabrous. Stems become woody as they age. The color of typical young stems and young lateral branches is R.H.S. 144 A (yellow-green group). The older portions of the stems are R.H.S. 199 A (grey-brown group). Younger portions of the stems are 7 mm in diameter. Older portions of the stems are 7 mm in diameter.

*Foliage.*—Abundant. Leaves are opposite on stem and lateral branches. Shape of leaf. — Elliptic with acute base and acute apex. Tips of leaves are 10 mm long. Margins are serrate and not lobed. Texture. — Glabrous; veins dominate on the underside of the leaf and are sunken on the upper leaf surface. The upper side of the leaf is moderately glossy. Variegation is absent. Color. — Mature leaves have an upper side that is R.H.S. 136 A (green group), and an under side that is R.H.S. 137 C (green group). Leaves are pinnately veined. The midvein and veins branching off the midvein are large and prominent on the underside of the leaves. Veins are R.H.S. 145 C (yellow-green group). Leaves are as wide as 10 cm and 15 cm long. Petioles are smooth and approximately 2 cm long and 4 mm wide. Petioles are R.H.S. 145 C (yellow-green group).

Buds:

*Form.*—Globose with 4 to 5 connate, elliptic, smooth petals. The terminal and later-developing buds of the panicles are non-sepalous. The majority of buds will develop into sepalous florets. The buds are approximately 2 mm by 2 mm when very young. Buds can be 5 mm in diameter and still unopened. Color of mature buds is R.H.S. 87 B (violet group) for the observed plants treated with aluminum. Color of mature buds is R.H.S. 70 C (red-purple group) for the observed plants that were not treated with aluminum.

*Aspect.*—Smooth.

*Arrangement.*—Borne on branched panicles.

Inflorescence:

*Form.*—Paniculate. Terminal. As many as 70 individual florets (both sepalous and non-sepalous) per inflorescence. Both sepalous florets and non-sepalous florets are borne on the same panicle. Non-sepalous florets are inconspicuous. Flowers do not produce a fragrance. The peduncle for the inflorescence is strong and upright. There are very few non-sepalous florets. The non-sepalous florets are located at the terminal portion of the panicle and are later hidden by sepalous florets. Florets, both sepalous and non-sepalous, have anthers and style. Inflorescences are long-lasting. Florets near terminal floret have less developed sepals and are less pigmented.

*Size of Inflorescence.*—Medium. Individual inflorescence size is dependent on the number of florets. A typical inflorescence can grow as large as 8" in diameter, and 4" high.

*Shape.*—Globose. Clusters of numerous small florets; sepalous florets overlap one another. Sepals are persistent.

*Appearance.*—Showy.

Florets:

*General.*—The non-sepalous florets at the center of the panciles open first. Sepalous and non-sepalous florets are perfect and complete. Corolla: Generally, for both sepalous and non-sepalous florets there are 4 to 5 petals. Petals are typically 4 mm long and 3 mm wide. Petals are R.H.S. 96 D (violet-blue group) for observed plants treated with aluminum. Petals are R.H.S. 87 B (red-purple group) for observed plants not treated with aluminum. Lenticels are present on pedicels of both sepalous and non-sepalous florets, lenticels and range in length from 1 mm to 3 mm. For plants treated with aluminum, lenticels are R.H.s. 80 A (purple-violet group). For plants not treated with aluminum, lenticels are R.H.S. 70 A (red-purple group). Pedicel length for non-sepalous florets averages 3 mm. Pedicel length of sepalous florets is approximately 30 mm in length for plants of this age. Pedicels of both sepalous and non-sepalous florets continue to elongate as the inflorescence ages. In the observed plants treated with aluminum, pedicels range from 78 C (purple group) at the base of the pedicel to R.H.S. 145 B (green group) near the floret when mature for observed plants treated with aluminum. In the observed plants not treated with aluminum, pedicels range from 70 C (red-purple group) at the base of the pedicel to R.H.S. 145 B (green group) near the floret when mature.

*Stamens.*—8 to 12 stamens. Anther is regular and basally attached. The stamens are 5 mm long and are R.H.S. 96 A (violet-purple group). The anthers are 2 mm long and are R.H.S. 145 A (yellow-green group). Pollen is scarce.

*Stigma.*—Two to four style each. Each style has one stigma.

*Ovary.*—Ovary is partially inferior.

*Sepalous florets.*—General. — Veins dominate on the underside of the sepals. Number of sepals. — 4 to 5 sepals per floret. Aspect of sepals. — Smooth and glaucescent. Shape of sepals. — Reniform with acuminate apex. Edges are entire, but with some crenation. Size of sepals. — As the florets mature, the sepals enlarge and overlap each other more and more, until, often, there is no space between the sepals when the petals of the florets open. Sepals at maturity are typically 40 mm long and 50 mm wide. Sepalous florets are typically 70 mm in diameter. In the observed plants treated with aluminum, the upper sides of the sepals are R.H.S. 71 A (red-purple group). In the observed plants treated with aluminum, the undersides are R.H.S. 72 B (red-purple group). In the observed plants not treated with aluminum, the upper sides of the sepals are R.H.S. 61 B (red-purple group). In the observed plants not treated with aluminum, the undersides are R.H.S. 70 C (red-purple group). Pigmentation-develops at the tips of the sepals and travels inward towards the base of the sepals.

*Fruit.*—None.

*Disease and Pest Resistance.*—Unknown.

*Plants prefer milder temperatures.*

*Plants bloom in the spring but can be forced to bloom by placing in a cold environment.*

I claim:

1. A new and distinct *Hydrangea macrophylla* plant named 'BCHY-15.008' substantially as herein illustrated and described.

* * * * *